United States Patent
Dolfi et al.

(10) Patent No.: US 10,172,691 B2
(45) Date of Patent: Jan. 8, 2019

(54) ORTHODONTIC EXPANDER

(71) Applicant: LEONE S.P.A., Sesto Fiorentino (IT)

(72) Inventors: Maurizio Dolfi, Florence (IT); Gabriele Scommegna, Tavarnuzze Impruneta (IT)

(73) Assignee: LEONE S.P.A., Sesto Fiorentino (IT)

(*) Notice: Subject to any disclaimer, the term of this patent is extended or adjusted under 35 U.S.C. 154(b) by 433 days.

(21) Appl. No.: 14/764,731

(22) PCT Filed: Dec. 17, 2013

(86) PCT No.: PCT/IT2013/000351
§ 371 (c)(1),
(2) Date: Jul. 30, 2015

(87) PCT Pub. No.: WO2014/122680
PCT Pub. Date: Aug. 14, 2014

(65) Prior Publication Data
US 2016/0008098 A1   Jan. 14, 2016

(30) Foreign Application Priority Data

Feb. 9, 2013   (IT) ................. FI2013A0028

(51) Int. Cl.
*A61C 7/10*   (2006.01)
(52) U.S. Cl.
CPC ..................... *A61C 7/10* (2013.01)
(58) Field of Classification Search
CPC ...................................... A61C 7/10
See application file for complete search history.

(56) References Cited

U.S. PATENT DOCUMENTS

| 5,405,614 | A | * | 4/1995 | D'Angelo | A61K 9/7023 |
| | | | | | 424/447 |
| 6,309,213 | B1 | * | 10/2001 | Forster | A61C 7/10 |
| | | | | | 433/7 |
| 6,425,758 | B1 | | 7/2002 | Foerster | |
| 2007/0218416 | A1 | * | 9/2007 | Keles | A61C 7/10 |
| | | | | | 433/7 |

(Continued)

FOREIGN PATENT DOCUMENTS

| DE | 15 66 260 A1 | 8/1970 |
| FR | 998 076 A | 1/1952 |
| GB | 718 385 A | 11/1954 |

*Primary Examiner* — Heidi M Eide
(74) *Attorney, Agent, or Firm* — McGlew and Tuttle, P.C.

(57) ABSTRACT

Orthodontic expander including a left frame (T1) and a right frame (T2). The left frame (T1) and right frame (T2) respectively include a left body (1) and a right body (2) provided with structure for their anchorage to the teeth of a dental arch. The bodies (1.2) have through holes (10) oriented in an expansion direction (d). The frames (T1, T2) are slidingly mounted along the expansion direction (d) by guides (4) inserted in the holes (10) of the bodies (1.2). The distance (h) between the bodies (1, 2) is adjusted by a screw (5) screwed into the body (2) of one of the frames. The screw (5) has an operating head (51) positioned between the bodies (1.2) Elastic plates are positioned and acting between the frames (T1, T2) and can be activated or reactivated by acting on the screw (5) which compresses them to activate or reactivate them when desired.

20 Claims, 7 Drawing Sheets

FIG.5

(56) References Cited

U.S. PATENT DOCUMENTS

2008/0119795 A1* 5/2008 Erskine ............ A61M 25/0618
604/192
2010/0086889 A1* 4/2010 Lindquist ................ A61C 7/04
433/4
2010/0112507 A1 5/2010 Ehrenberger et al.

* cited by examiner

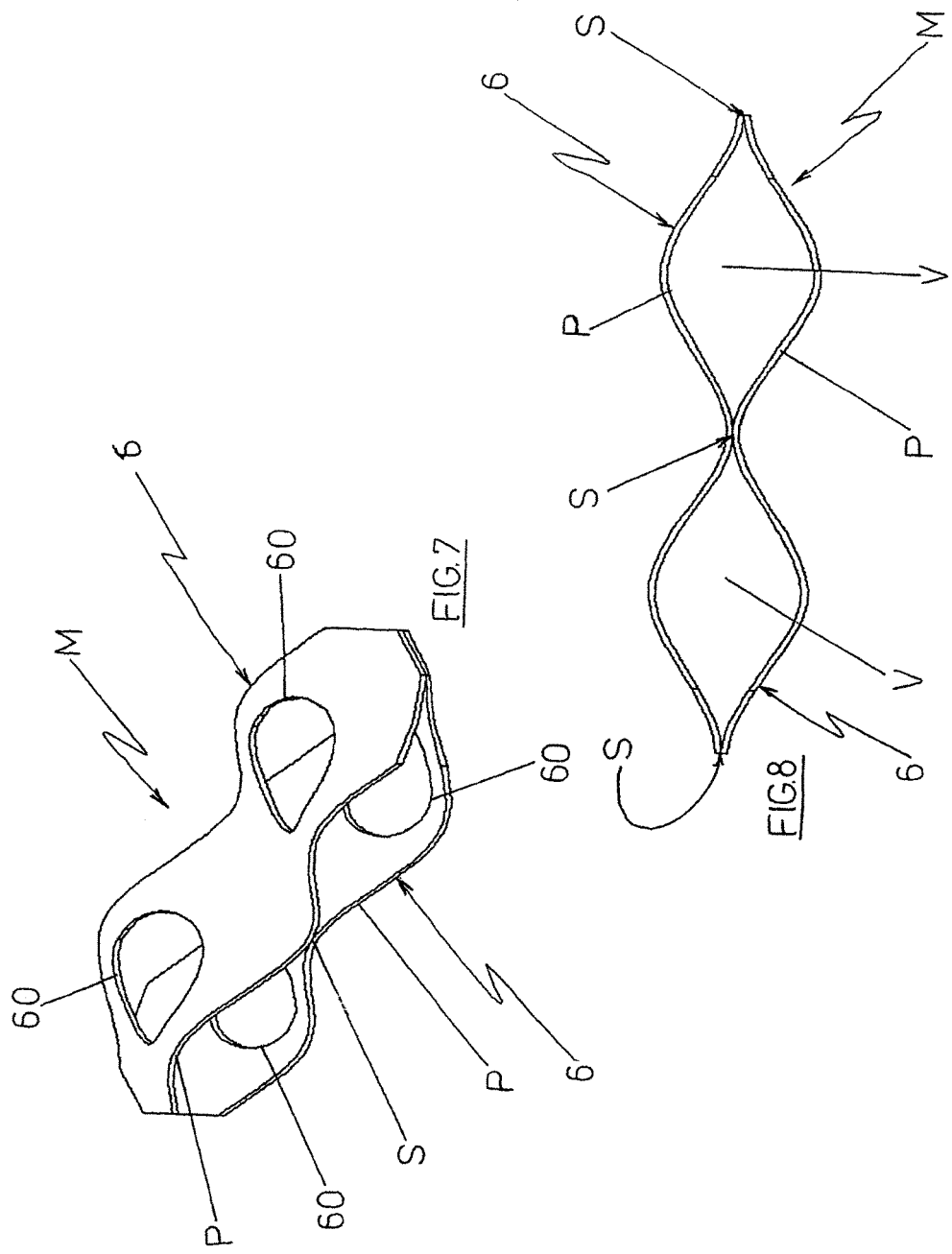

ORTHODONTIC EXPANDER

The present invention relates to an orthodontic expander.

It is known that an orthodontic expander is an intraoral device used for correcting the negative effects of transverse maxillary growth deficiency by the application of forces destined to increase the width of the dental arch in the transverse direction.

In general, an orthodontic expander consists of two bodies, respectively connected to dental elements of the right side and the left side of the dental arch by means of anchoring arms that are connected to each other by a central screw. Between those two bodies is placed a coil spring which is compressed or "loaded" by the dentist through the center screw each time that the coil spring action is exhausted.

The thrust exerted by the spring on the two bodies of the device is transmitted to the two corresponding sides of the dental arch thus determining, in a relatively long time and with the periodic charging of the spring, the desired expansion. The said spring is oriented parallel to the expansion direction, i.e. orthogonally to the two bodies that are connected to the teeth of the dental arch.

The orthodontic expanders are intended to be inserted in under-developed oral cavities and the length of the said coil spring cannot be excessive given the small space available, and it is still strongly felt the need of having alternative construction systems providing a reduction of the overall size of orthodontic expander without reducing the operational capacity thereof.

Another problem related to the use of orthodontic expanders of the type mentioned above is related to the fact that the spring positioned between said bodies is encapsulated and therefore is not visible, so that the dentist cannot visually check the state of compression of the spring.

The main purpose of the present invention is to overcome the aforesaid drawbacks.

This result is achieved, according to the present invention, by adopting the idea of making an orthodontic expander having the characteristics indicated in claim 1. Other features of the present invention are the subject of the dependent claims.

Thanks to the present invention, it is possible to realize a more efficient orthodontic expander and the dentist has the opportunity to visually check the state of compression of the spring. Moreover, the orthodontic expander is relatively cheap in relation to the advantages it offers.

These and other advantages and features of the present invention will be best understood by anyone skilled in the art thanks to the following description and to the attached drawings, given by way of example but not to be considered in a limiting sense, in which:

FIG. 7 is a front perspective view of a further embodiment of a leaf spring of the orthodontic expander shown in FIG. 1;

FIG. 8 is a side view of the leaf spring shown in FIG. 7.

Figure 1:
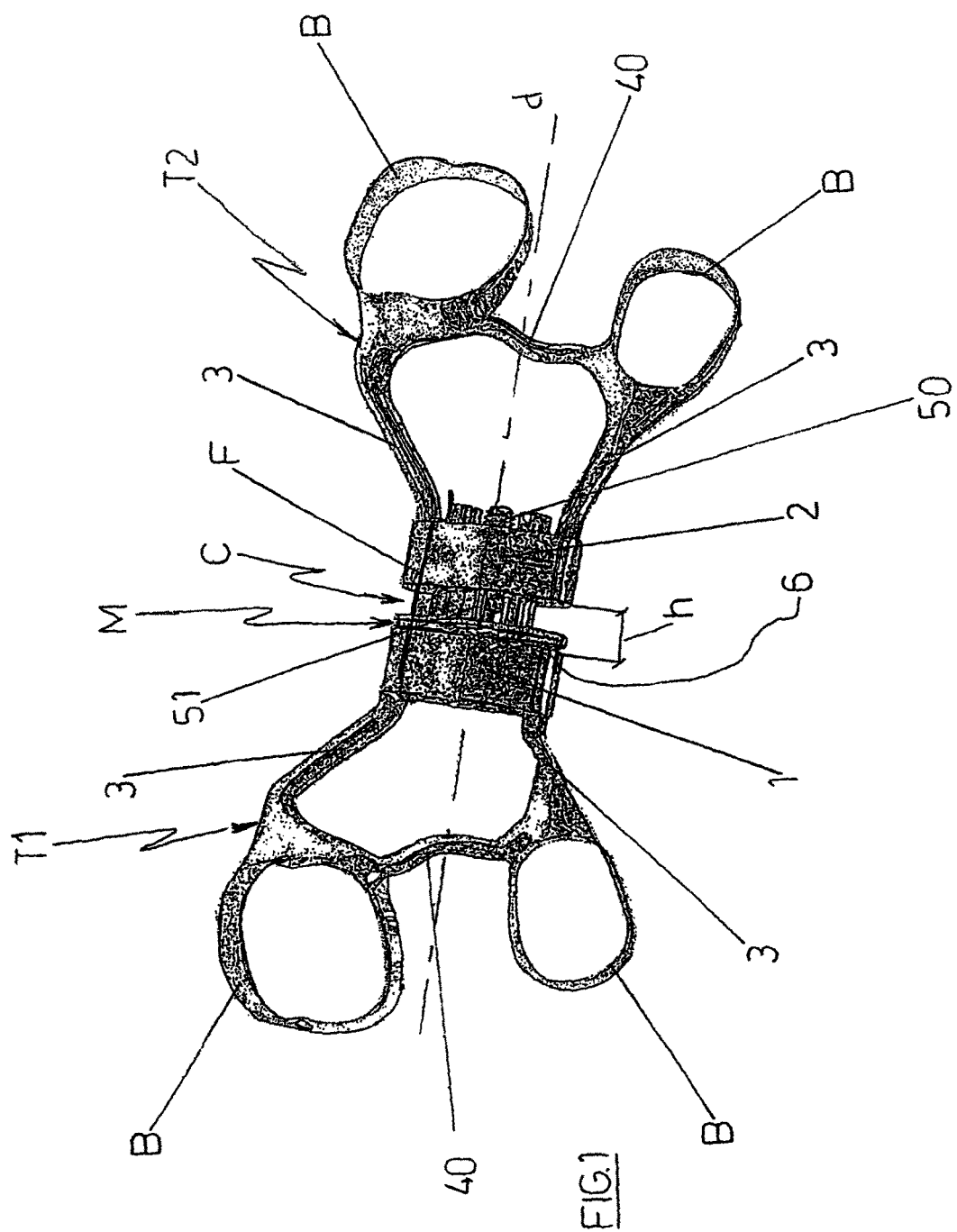
FIG. 1 is a front perspective view of an orthodontic expander in accordance with the present invention.

Reduced to its essential structure, and with reference to the figures of the attached drawings, an orthodontic expander in accordance with the present invention comprises two bodies, one of which is on a left side (1) while the other is on the right side (2), each of said bodies being connected to two annular bands (B) by means of a corresponding pair of longitudinal arms (3).

The two annular bands (B) attached to each body (1,2) are joined together by a transverse arm (40). In practice, each body (1) or (2) forms a left frame (T1) and, respectively, a right frame (T2) with the corresponding longitudinal arms (3), transverse arms (40) and annular bands (B). The two frames (T1, T2) can be made, for example, of stainless steel. The left (T1) and right (T2) frames are fixed respectively to the left and right sides of a patient's upper dental arch and then cemented by fitting each of the corresponding bands (B) on one of the teeth of the same dental arch selected by the dentist. To this end, each band (B) has a size and shape determined according to the shape of the tooth onto which it must be cemented. Each frame (T1, T2) has a predetermined size and shape according to the anatomical conformation of the left side or right side of the palate in which it must be accommodated.

After the attachment of the bands (B) to the selected teeth of the upper arch, each body (1,2) is fixed, by means of the corresponding pair of longitudinal arms (3), to a corresponding left or right side of the upper dental arch.

The left (T1) and right (T2) are frames connected together by a pair of grinded rods or guides (4) that are parallel to each other and circular in cross section. Each rod (4) has predetermined dimensions, is fixed for a predetermined length in a hole (10) of the body left (1) and passes through a hole (10) of the right body (2) which, therefore, can slide on the same rod (4). Therefore, the rods (4) act as guides for the right body (2) that, in this way, can translate along a direction (d) set by the same rods (4); in other words, the right body can be moved towards and from the left body (1) along the said direction (d). The direction (d) is predetermined and coincides with that of the loads to be applied to left and right sides of the upper dental arch, as further described below. The direction (d) is parallel to the longitudinal axes of the rods (4).

Each body (1,2) has two transverse flat surfaces, i.e. one on its right side (S2) and the other on the left side (S1), that are parallel to each other and both perpendicular to the axes of said holes (10).

Then, when the right body (2) is positioned on the rods (4) it features the corresponding transverse flat surfaces (S1, S2) arranged parallel to those of the left body (1). It is thus formed a seat (C) of height (h) between the left surface (S1) of the right body (2) and the right surface (S2) of the left body (1) facing each other. Being the right body (2) slidingly positioned on the rods (4), the length (h) of said seat (C) is variable. In particular, the length (h) varies between two values, one of which is a minimum value (h1) and the other is a maximum value (h2) respectively corresponding to the initial and final configurations of the expander as further described below.

Between the two bodies (1,2) there is the operating head (51) of a screw (5). The shank (50) of the same screw (5) is screwed into the right body (2) in a corresponding threaded through hole whose axis is perpendicular to the said surfaces (S1, S2) of the same right body (2), i.e. is parallel to the guides (4). The said head (51) is arranged with a respective flat surface parallel to the counter-facing right surface (S2) of the left body (i) and is arranged between the two rods (4) that, advantageously, have grooves (41) allowing it to be properly accommodated in order to provide greater transverse compactness to the expander, albeit making use of a head (51) whose size is sufficient to allow the intervention of the dentist on the screw (5) as described below.

Between the head (51) of the screw (5) and the left body (i) there are provided elastic means (M) of predetermined stiffness and deformable along the direction (d) of sliding of the right body (2).

Figure 2:
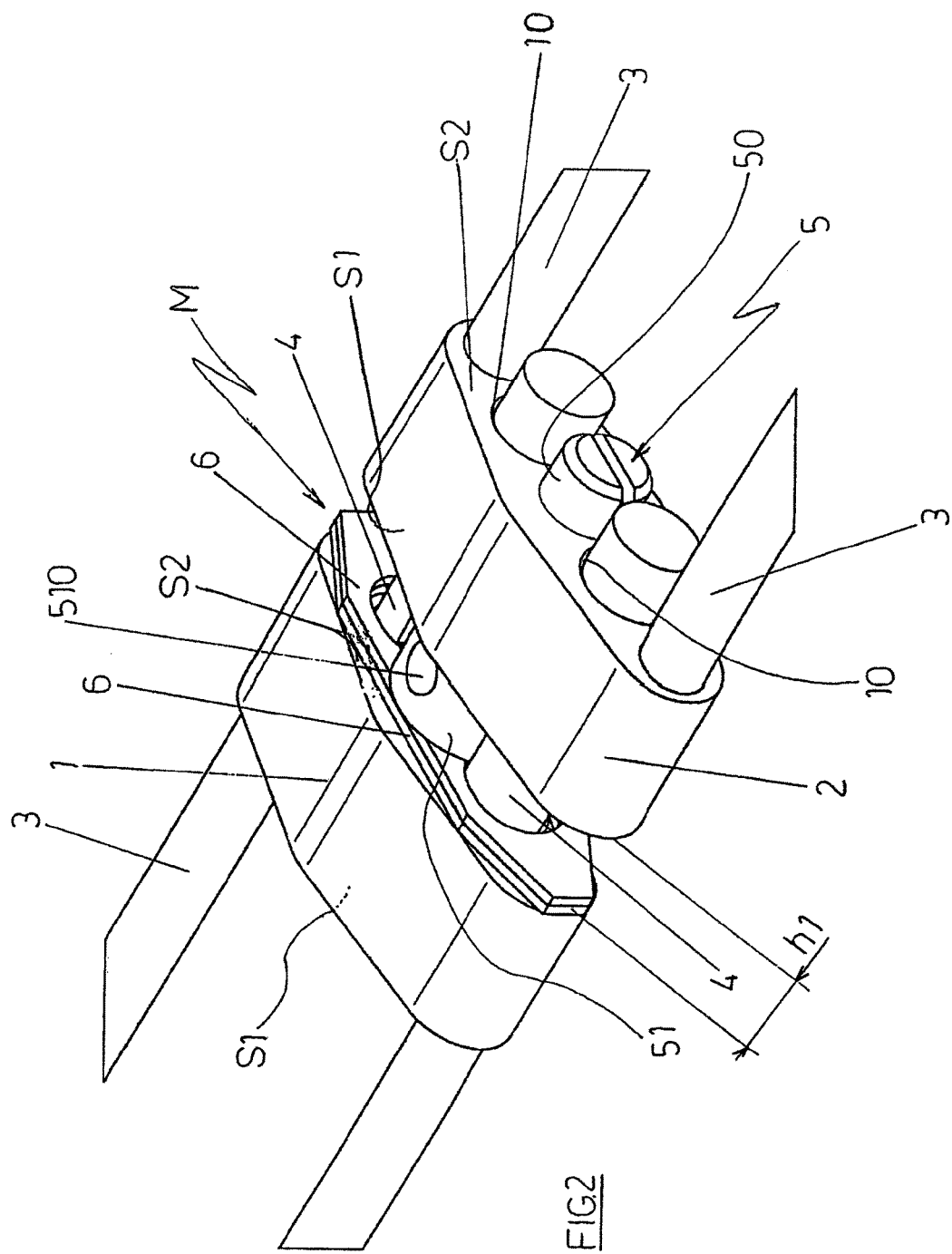
FIG. 2 is a front perspective view of a push assembly of the expander shown in FIG. 1 in an initial loaded configuration.
Figure 3:
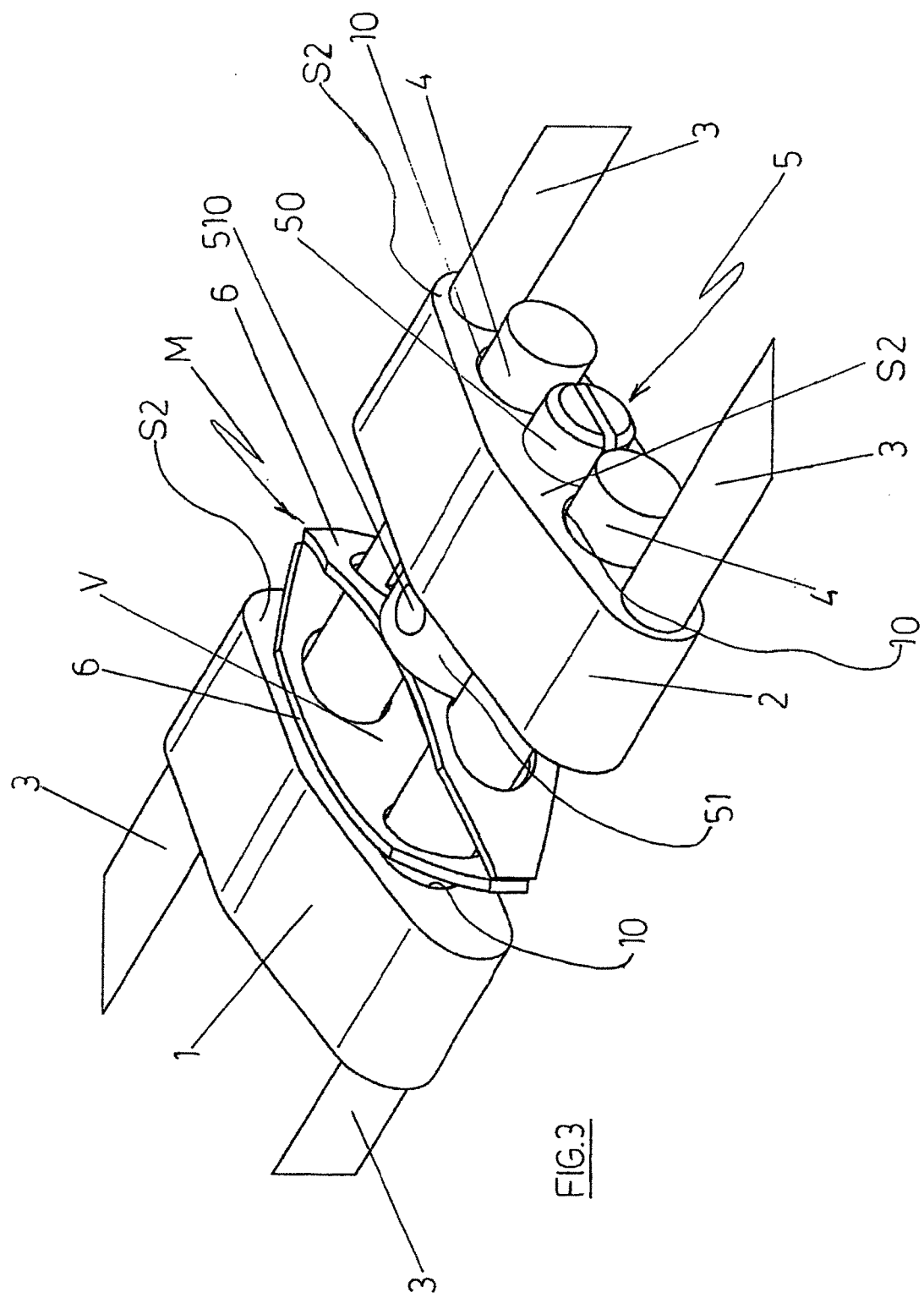
FIG. 3 is a front perspective view of the push assembly of FIG. 2 in an initial unloaded configuration.
Figure 4:
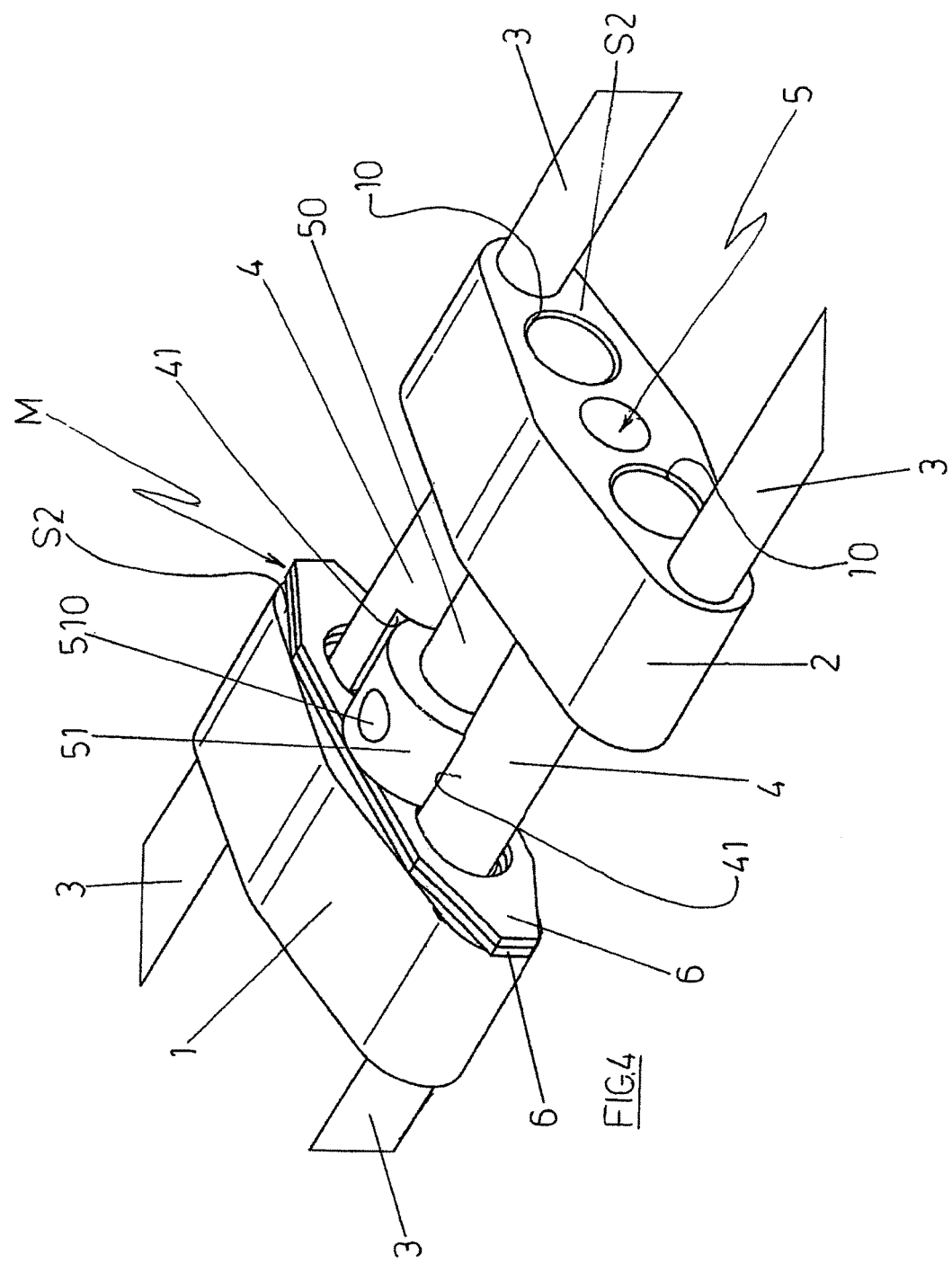
FIG. 4 is a front perspective view of the push assembly of FIG. 2 in a final loading configuration.
Figure 5:
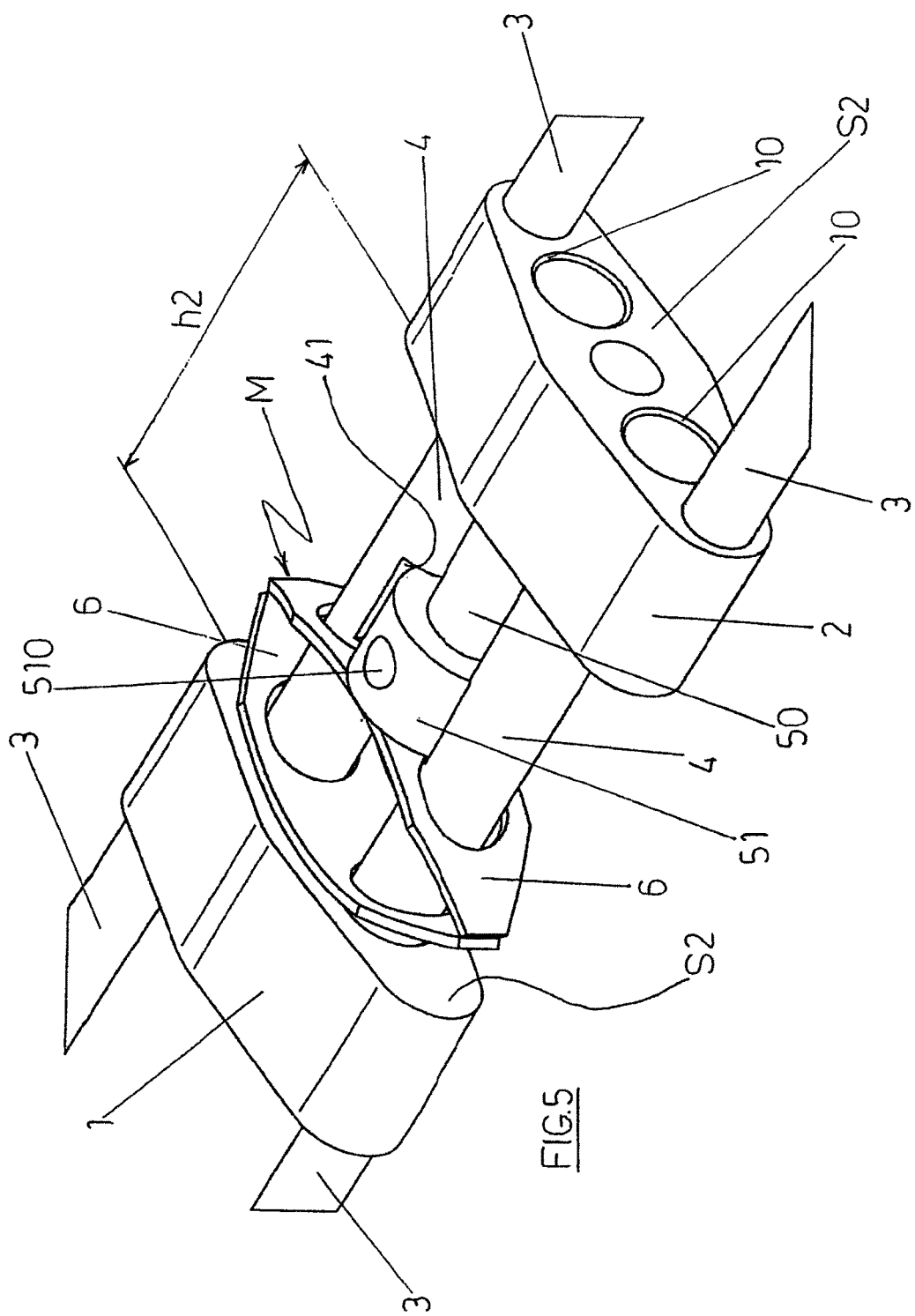
FIG. 5 is a front perspective view of the push assembly of FIG. 2 in a final unloaded configuration.
Figure 6:
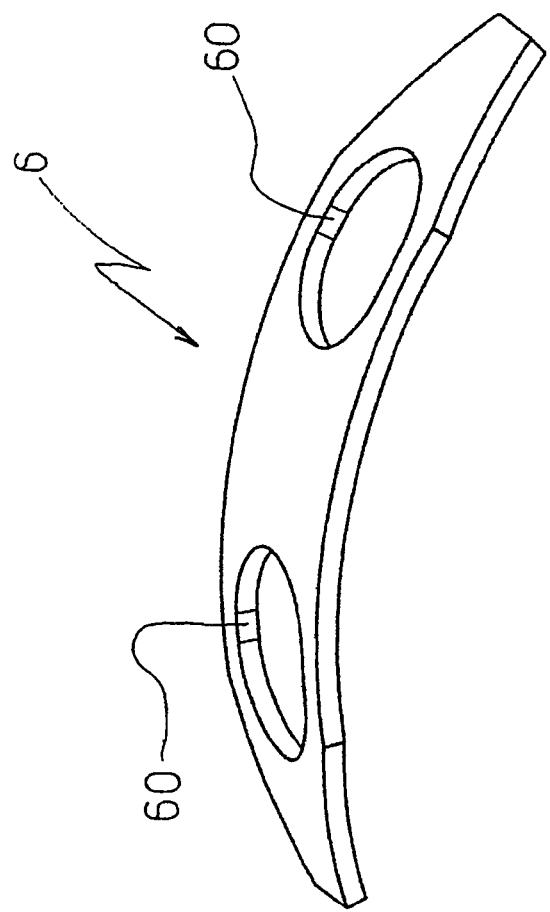
FIG. 6 is a front perspective view of a leaf spring of the orthodontic expander of FIG. 1.

According to the example shown in FIGS. 2-6, said elastic means (M) consist of two plates (6) with arcuate profile (P), arranged with their respective ends in reciprocal contact and with the respective concavities facing each other so as to include, in a non-compressed or partially compressed configuration, a volume (V) whose value varies according to the compression of the same plates (6).

Each of said plates (6) has a pair of elliptical holes (60) through which the rods (4) are made to pass. The holes (60) are elliptical, instead of being circular, allow each plate (6), in the compression phase, to deform freely along the sliding direction (d) of the right body (2) without interfering with the rods (4) passing therethrough.

Said plates (6) can be made for example of nickel-titanium alloy.

Alternatively, as shown in FIGS. 7 and 8, the plates (6) may have a serpentine profile (P), such that, once packed between the left body (1) and said head (51), in a rest or in a partial compression state, the same plates have at least two points (S) in reciprocal contact so as to include at least one volume (V) of predetermined size and shape that, however, can vary to allow the same plates (6) to deform to a given extent along the sliding direction (d) of the right body (2).

According to a further embodiment of the present invention, each plate (6) can be doubled, so as to provide two packed plates instead of a single one. Said operating head (51) has a radial passing hole (510) in which it is possible to insert the tip of a tool to cause rotation of the screw (5) in the desired direction so as to adjust the compression force of the plates (6 increasing or decreasing it, respectively, by screwing or unscrewing the stem (50) of the screw (5) in the right body (2).

The plates (6), when compressed, exert an expansive force on the left body (1) and an opposite expansive force on the right body (2), both the expansive forces being oriented along said direction (d). therefore, by compressing the plates (6), the left frame (T1) and the right frame (T2) exert said expansive forces respectively on the left and right side of the dental arch subjected to the orthodontic treatment.

According to the example described above, the elastic means (M), the screw (5), the bodies (1, 2) and the rods (4) constitute the push assembly of the present screw-operated orthodontic expander.

Advantageously, according to the present invention, instead of having one or more coil spring as in conventional screw-operated orthodontic expanders, the elastic means (M) is made by an assembly comprising a plurality of plates (6), the plates (6) being oriented transverse to the guides (4), i.e. orthogonal to the said direction (d).

The use of plates (6) instead of coil springs provides more compactness which is a great advantage for the positioning of the orthodontic expander in the patient's oral cavity, considering that the available space between the left and right sides of the patient's dental arch is limited (in fact, the orthodontic expander is used to increase said space). To this end, the plates (6) are oriented transverse to the guides (4), i.e. transverse to the said direction (d).

Furthermore, the plates (6) are positioned in a visible way, in the space between the bodies (1) and (2) of the expander, thereby allowing the dentist to easily check the compression state of the same plates.

In the foregoing description the terms "left" and "right", " left body " and "right body" refer to the examples shown in the attached drawings, but should not be construed in a limiting sense.

The following description refers to a possible use of an orthodontic expander according to the invention.

The expander is positioned on the patient's upper dental arch in an initial loaded configuration, i.e. with the stem (50) of the screw (5) screwed in the right body (2) and with the plates (6) compressed by means of a ring-shaped wire (F) that in this step joins the left and right bodies (1, 2) so as to neutralize the effect of the push exerted by the plates (6). In this state, the length (h1) of said seat (C) is minimum, this minimum value being at least equal to the height of the operating head (51) of the screw (5) plus the thickness of the plates (6) in the compressed state.

After having mounted the expander on the patient's upper dental arch, the wire (F) is cut so that the plates (6) are free to apply, through the left frame (T1) and the right frame (T2), the said expansive forces on the left and right sides of the dental arch.

Over time, by effect of the push exerted by the plates (6), the dental structures to which the expander is joined are subjected to expansion and the plates (6) gradually flex and become unloaded, i.e. said plates assume a configuration in which they are no more able to apply a significant expansion force on the upper dental arch. Thus, the expander assumes an unloaded configuration. In this unloaded configuration the plates (6) assume the arcuate configuration shown in FIGS. 5-8.

In order to reactivate the expander, the screw (5) is unscrewed from the body right (2) by turning the respective head (51) by means of a tool (not shown in the drawings) and thus compressing the plates (6).

Since the plates (6) are visible, it is possible to check their state of compression, unlike the expanders of the prior art in which a not visible encapsulated coil spring is generally used.

The loading operation described above is performed a predetermined number of times, until reaching the final configuration (maximum expansion permitted) of the expander, in which the seat (C) presents the previously mentioned maximum length (h2), which corresponds to desired opening of the upper dental arch. Subsequently, or even earlier depending on the clinical evaluations of the dentist, the expander can be removed from the dental arch similarly to what is done for conventional orthodontic expanders.

In practice, the details of execution may vary in any equivalent way as in the shape, size, nature, type and arrangement of the elements indicated, without leaving the scope of the adopted solution and thus remaining within the limits of the protection granted to the present patent.

The invention claimed is:

1. An orthodontic expander comprising:
    a left frame and a right frame, wherein said left frame comprises a left body and said right frame comprises a right body, each of said left body and said right body comprising an anchoring means for anchoring said left body and said right body to the teeth of a dental arch, wherein each of said left body and said right body has through holes oriented in an expansion direction, wherein said left frame and said right frame are slidingly mounted along said direction of expansion by means of guides inserted in said through holes of said left body and said right body, wherein a distance between said left body and said right body is adjusted by means of a screw screwed into one of the left body and the right body, wherein said screw has an operating head positioned between said left body and said right body, wherein an elastic means is positioned and acts between said left frame and said right frame and said elastic means can be activated or reactivated by acting on said screw which compresses said elastic means to activate or reactivate said elastic means when desired, said elastic means comprising a plurality of elastic plates with a curvilinear profile oriented transversely with respect to said direction of expansion, wherein a space is provided between said left body and said right body, said elastic means being positioned in said space.

2. An orthodontic expander according to claim 1, wherein said plurality of elastic plates comprises only a first elastic plate with a first plate curved profile and a second elastic plastic with a second plate curved profile, said first plate and said second plate being arranged with respective ends in contact and with respective concavities facing one another so as to comprise, in a configuration not compressed or partially compressed, a volume of variable size in function of a magnitude of compression to which the first plate and the second plate are subjected.

3. An orthodontic expander according to claim 1, wherein said plurality of elastic plates are constrained to said guides.

4. An orthodontic expander according to claim 3, wherein said plurality of elastic plates have a pair of elliptical holes crossed by said guides.

5. An orthodontic expander according to claim 1, wherein each of said plurality of elastic plates has a profile comprising two consecutive concavities.

6. An orthodontic expander according to claim 1, wherein said anchoring means are made by orthodontic bands.

7. An orthodontic expander according to claim 1, wherein at least one of said plurality of elastic plates is provided between said operating head and one of said left body and said right body.

8. An orthodontic expander according to claim 1, wherein one of said plurality of elastic plates is in direct contact with said operating head.

9. An orthodontic expander according to claim 7, wherein said at least one of said plurality of elastic plates is in direct contact with said operating head.

10. An orthodontic expander comprising:
a first frame comprising a first frame body and a first frame anchoring means for fixing said first frame body to at least one tooth, said first frame body comprising first frame body through holes oriented in an expansion direction;
a second frame comprising a second frame body and a second frame anchoring means for fixing said second frame body to one or more teeth, said second frame body comprising second frame body through holes oriented in the expansion direction, wherein a space is provided between said first frame body and said second frame body;
a screw comprising an operating head, said screw being in contact with one of said first frame body and said second frame body, said operating head being located between said first frame body and said second frame body;
guides inserted in said first frame body through holes and said second frame body through holes, said first frame body and said second frame body being slidingly mounted along said direction of expansion via said guides, wherein a distance between said first frame body and said second frame body is adjusted via said screw;
a plurality of elastic plates positioned and acting between said first frame and said second frame, wherein said plurality of plates are activated or reactivated via actuation of said screw, each of said plurality of elastic plates comprising a curvilinear profile oriented transversely with respect to said direction of expansion, each of said plurality of elastic plates being arranged in said space.

11. An orthodontic expander according to claim 10, wherein each of said plurality of elastic plates comprises a serpentine profile with two consecutive concavities.

12. An orthodontic expander according to claim 10, wherein said plurality of elastic plates are arranged between said operating head and one of said first frame body and said second frame body.

13. An orthodontic expander according to claim 12, wherein one of said plurality of elastic plates is in direct contact with said operating head, wherein one of said first frame body and said second frame body is located at a spaced location from said operating head and another one of said first frame body and said second frame body being located adjacent to said operating head.

14. An orthodontic expander according to claim 12, wherein said operating head is located in said space.

15. An orthodontic expander according to claim 10, wherein one of said plurality of elastic plates is in direct contact with said operating head.

16. An orthodontic expander comprising:
a first frame comprising a first frame body and a first frame anchoring means for fixing said first frame body to at least one tooth, said first frame body comprising first frame body through holes oriented in an expansion direction;
a second frame comprising a second frame body and a second frame anchoring means for fixing said second frame body to one or more teeth, said second frame body comprising second frame body through holes oriented in the expansion direction, wherein a space is provided between said first frame body and said second frame body;
a screw comprising an operating head, said screw being in contact with one of said first frame body and said second frame body, said operating head being located between said first frame body and said second frame body;
a first guide inserted in a first one of said first frame body through holes and a first one of said second frame body through holes;
a second guide inserted in a second one of said first frame body through holes and a second one of said second frame body through holes, said first frame body and said second frame body being slidingly mounted along said direction of expansion via said first guide and said second guide, wherein a distance between said first frame body and said second frame body is adjusted via said screw;
a plurality of elastic plates positioned and acting between said first frame and said second frame, wherein said plurality of plates are activated or reactivated via actuation of said screw, each of said plurality of elastic plates comprising a curvilinear profile oriented transversely with respect to said direction of expansion, each of said plurality of elastic plates being arranged in said space.

17. An orthodontic expander according to claim 16, wherein each of said plurality of elastic plates is provided between said operating head and one of said first frame body and said second frame body.

18. An orthodontic expander according to claim 16, wherein one of said plurality of elastic plates is in direct contact with said operating head.

19. An orthodontic expander according to claim 16, wherein said operating head is located in said space.

20. An orthodontic expander according to claim 16, wherein each of said plurality of elastic plates comprises a profile comprising two consecutive concavities.

\* \* \* \* \*